United States Patent [19]

Morishita

[11] Patent Number: 4,753,222

[45] Date of Patent: Jun. 28, 1988

[54] ENDOSCOPIC FLEXIBLE TUBE

[75] Inventor: Koji Morishita, Tokyo, Japan

[73] Assignee: Olympus Optical Co., Ltd., Japan

[21] Appl. No.: 937,974

[22] Filed: Dec. 4, 1986

[30] Foreign Application Priority Data

Dec. 13, 1985 [JP] Japan .................. 60-280502

[51] Int. Cl.⁴ .............................. A61B 1/00
[52] U.S. Cl. .............................. 128/4
[58] Field of Search ................ 128/4, 6

[56] References Cited

U.S. PATENT DOCUMENTS 3,670,721 6/1972 Fukami et al. ............ 128/6
3,960,143 6/1976 Terada ..................... 128/4

FOREIGN PATENT DOCUMENTS 3242449 5/1983 Fed. Rep. of Germany .
55112505 1/1954 Japan .
56-101301 10/1981 Japan .

Primary Examiner—William H. Grieb

[57] ABSTRACT

Disclosed is a construction of a flexible tube, which is applied to an insertion section of an endoscope, adapted to be inserted into the body cavity. The flexible tube comprises a spiral tube formed by transforming a belt-shaped metal member into a spiral, a braid formed of fibers intertwined like a net, and fitted on the outer peripheral surface of the spiral tube, and a sheath covering the outer peripheral surface of the braid, and having a multilayer structure composed of inner and outer layers, at least for part of its length. The inner layer is a tube member which is formed of a high-polymer material, and is fitted on the outer peripheral surface of the braid. The outer layer is formed by applying a molten high-polymer material to the outer peripheral surface of the tube member, for cross-linking.

6 Claims, 4 Drawing Sheets

F I G. 3
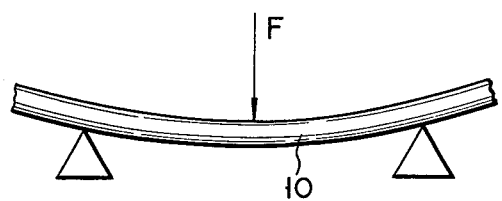
F I G. 4
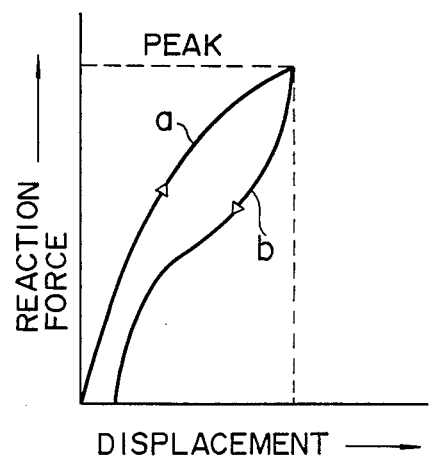

ENDOSCOPIC FLEXIBLE TUBE

BACKGROUND OF THE INVENTION

A. Field of the Invention

The present invention relates to an insertion section of an endoscope adapted to be inserted into the body cavity, and more specifically, to a flexible tube for use in the insertion section.

B. Description of the Prior Art

A typical endoscope comprises a distal section, insertion section, and operating section. The distal section is formed with openings for a view window, illumination window, and instrument channel. The insertion section includes a flexible tube portion and a remote-controlled bending portion, while the operating section includes a bending mechanism portion and an eyepiece portion. The endoscope contains therein the instrument channel and an optical fiber bundle for observation. An operator can insert the distal section, along with the insertion section, into the body cavity, observe the affected part of a patient's body, and give necessary medical care.

Conventionally known are endoscopes which are adapted individually for observation of internal organs, such as the gullet, stomach, duodenum, small intestine, colon, etc. In endoscopes applied to the observation of the duodenum, small intestine, or colon, in particular, the insertion section is inserted deep into the body cavity. It has been confirmed clinically that the flexibility of the insertion section greatly influences the ease of insertion thereof, and hence, reduces the degree of pain suffered by the patient.

Stated in Japanese Utility Model Disclosure (Kokai) No. 56-101301, for example, is a prior art method of improving the ease of insertion of an insertion section, used in an endoscope, thereby reducing the pain experienced by the patient. A flexible tube is used in the insertion section, and it has a two-layer structure as part of its sheath. The distal portion of the flexible tube is relatively rigid, so that the insertion section can be easily inserted into the body cavity. In an endoscope flexible tube stated in Japanese Utility Model Disclosure (Kokai) No. 55-112505, moreover, the sheath of the tube has a two-layer structure, composed of soft and rigid layers. The thickness of the rigid layer reduces gradually from the operating-section to the distal end.

Thus, in the conventional endoscopic flexible tubes, all or part of the sheath has a two-layer structure, which improves the flexibility of the sheath. Accordingly, insertion of the insertion section is relatively easy, so that the patient suffers less pain when the endoscope is operated in his body. Nothing has been improved, however, with regard to the elasticity of the insertion section, which influences the ease of the insertion most. It is therefore relatively hard to insert the insertion section of the prior art endoscopes into the body cavity. In consequence, the patient cannot be fully protected from pain when he is subjected to an endoscopic diagnosis or examination.

SUMMARY OF THE INVENTION

The object of the present invention is to improve the elasticity of a flexible tube applied to an insertion section of an endoscope, thereby facilitating insertion of the insertion section into the body cavity, so that the patient can be protected from excessive pain when he is subjected to an endoscopic diagnosis or examination.

The above object of the invention is achieved by an endoscopic flexible tube, which comprises a spiral tube, formed by transforming a belt-shaped metal member into a spiral; a braid formed of fibers intertwined like a net, and fitted on the outer peripheral surface of the spiral tube; and a sheath covering the outer peripheral surface of the braid, and having a multilayer structure composed of at least inner and outer layers, at least for part of its length, the inner layer including a tube member formed of a high-polymer material, and fitted on the outer peripheral surface of the braid, and the outer layer being formed by applying a molten high-polymer material to the outer peripheral surface of the tube member, for cross-linking.

BRIEF DESCRIPTION OF THE DRAWINGS

FIG. 3 is a perspective view for schematically illustrating an elasticity test on a conventional endoscopic flexible tube;

FIG. 4 is a graph showing relations between displacement and reaction force, obtained when the conventional flexible tube is pushed into the body cavity;

DETAILED DESCRIPTION OF THE PREFERRED EMBODIMENTS

Figure 1:
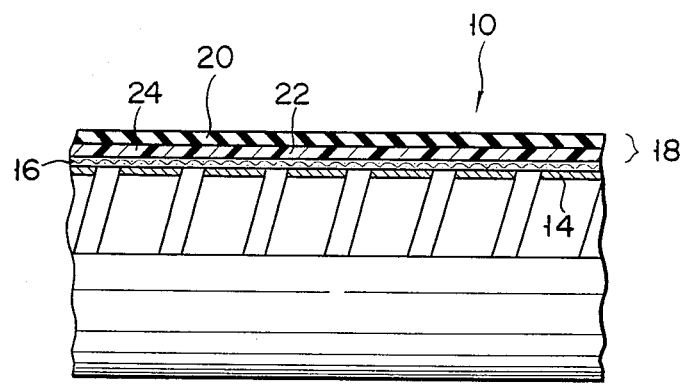
FIG. 1 is a sectional view showing part of an endoscopic flexible tube according to an embodiment of the present invention.
Figure 2:
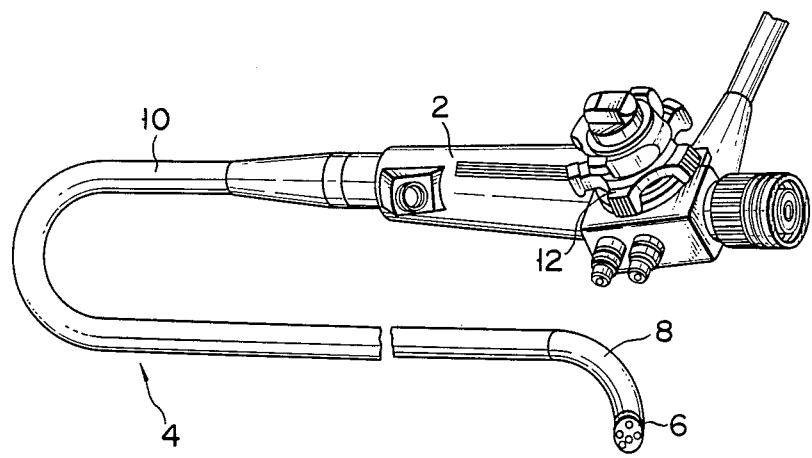
FIG. 2 is a perspective view of an endoscope according to the invention.

FIGS. 1 and 2 show an embodiment of the present invention, in which FIG. 2 is a general perspective view of an endoscope. Referring first to FIG. 2, an outline of the endoscope will be described in brief. The endoscope comprises operating section 2 for operating several mechanisms in the endoscope, insertion section 4, adapted to be inserted into the body cavity, and distal section 6. Section 4 includes bending tube portion 8 and flexible tube portion 10. Portion 8 is bent by operating angle knob 12, which is attached to section 2. As shown in FIG. 1, flexible tube portion 10 of the endoscope includes spiral tube 14, braid 16, and sheath 18. Tube 14 is a metal strip which is shaped like a spiral. Braid 16, which is formed of a network of fibers, is fitted on tube 14, and sheath 18 covers braid 16.

Sheath 18 has a two-layer structure, composed of outer and inner layers 20 and 22. Inner layer 22 includes tube member 24, which is formed of a high-polymer material, such as synthetic resin, synthetic rubber, etc. Member 24 is force-fitted on braid 16. Outer layer 20 is formed by applying molten high-polymer material to the outer peripheral surface of tube member 24, and then cross-linking the materials. A molding machine or die assembly is used for this process. In this manner, layer 20 is formed on the outer peripheral surface of member 24, which is previously fitted on braid 16. Since the high-polymer material is not applied directly to braid 16, it cannot soak into spiral tube 14 or braid 16.

Thus, if flexible tube portion 10 is bent, spiral tube 14 and braid 16 move smoothly, thereby ensuring improved elasticity of portion 10.

FIG. 4 is a graph showing relations between displacement and reaction force in the endoscopic flexible tube with the aforementioned construction. These relations are obtained when force F is applied to part of flexible tube portion 10 within a predetermined span, to depress portion 10 for a predetermined distance, as shown in FIG. 3, and then portion 10 is restored. In this graph, curve (a) represents the relation between displacement and reaction force obtained when portion 10 is depressed, while curve (b) indicates the relation obtained when portion 10 is restored to its original state. The rate of loss of the elasticity of flexible tube portion 10, calculated on the basis of the hysteresis of these curves, is $$1 - \frac{\text{Restoration curve }(b)}{\text{Depression curve }(a)}$$

The general elasticity of the flexible tube is evaluated in accordance with this value. As compared with the elasticity of prior art endoscopic flexible tubes, ranging from 0.2 to 0.3, the elasticity of the flexible tube of the present invention is 0.1 or less. This is because the restoring force of spiral tube 14 and braid 16 cannot be hampered by any undesired high-polymer material.

If tube member 24 is thin-walled, it can be force-fitted with ease, thus improving the manufacturing efficiency. Since outer layer 20 is formed by applying molten high-polymer material to member 24, the elasticity and flexibility of flexible tube portion 10 can be adjusted easily by reapplying the high-polymer material after completing portion 10.

The elasticity of flexible tube portion 10 can be improved by the use of the above described arrangement. Thereupon, an operator's push-in force on insertion section 4 is transmitted to distal section 6 through the flexible tube portion, without pressing too hard against any internal organs of a patient. Thus, the insertion section can be inserted easily into the body cavity.

Figure 5:
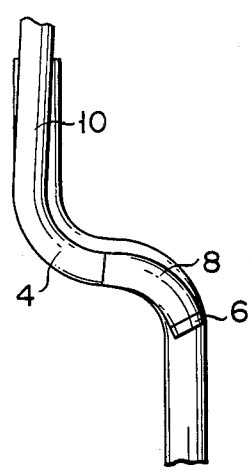
FIGS. 5 to 8 are diagrams showing the ways the endoscopic flexible tube of the invention and the conventional flexible tube are actually inserted into the body cavity.
Figure 7:
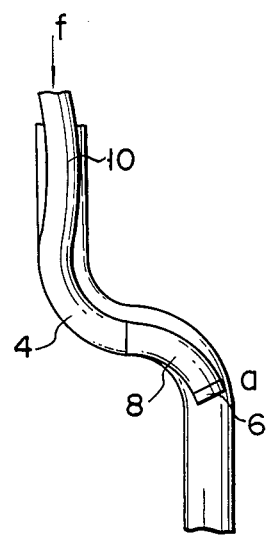
Figure 6:
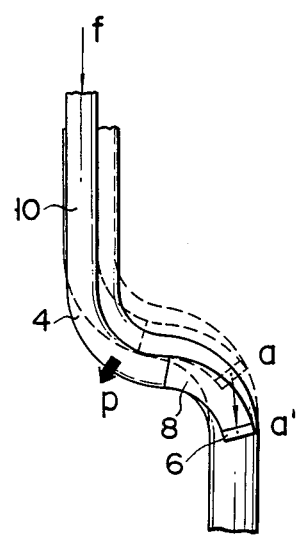
Figure 8:
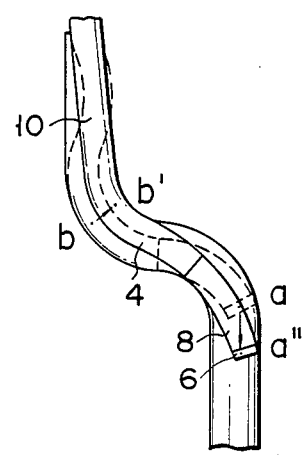

Referring now to FIGS. 5 to 8, the way of inserting the insertion section will be illustrated by example. In FIG. 5, insertion section 4 is in a curving body cavity, so that distal section 6 is caught by the body wall. If flexible tube portion 10 is too rigid, push-in force (f) of the operator is transmitted to distal section 6 when it is applied to flexible tube portion 10 in the position shown in FIG. 5. As a result, section 6 advances from point (a) to (a'), whereupon it presses hard against the body wall, acting in the direction of arrow P, as shown in FIG. 6. This causes substantial pain to the patient. If tube portion 10 is too soft, on the other hand, distal section 6 is caught by point (a) and cannot advance therefrom, as shown in FIG. 7, when the operator applies force (f) to tube portion 10. Thus, portion 10 becomes curved, as shown in FIG. 7. If the flexible tube is highly elastic as shown in FIG. 8, however, its distal end can be disengaged from point (a) by oscillating insertion section 4. At the same time, flexible tube portion 10 is restored from position (b) to (b') by its elasticity, so that distal section 6 advances from point (a) to (a''), as a reaction. Accordingly, push-in force (f) of the operator is transmitted to the distal end of the flexible tube, without pressing hard against the internal organs of the patient's body. Thus, the highly elastic flexible tube can be inserted easily into the body cavity, inflicting less pain on the patient.

In this embodiment, inner and outer layers 22 and 20 of sheath 18 are formed of polyester and polyurethane, respectively. Therefore, the outer surface of the sheath, made of polyurethane, cannot be damaged easily, and can be printed easily. The present invention is not, however, limited to the embodiment described above, and outer layer 20 may be formed also from polyolefin, polyvinyl chloride, chlorinated polyethylene, etc. Moreover, polyamide resin may be used for inner layer 22.

The outer and inner layer may be formed from any materials which exhibit elasticity at temperatures near the room temperature, and can be molded by extrusion. These materials include, for example:
 a. Polyester elastomer: Hitorel (tradename; Du Pont), Perplene (tradename; Toyobo);
 b. Thermoplastic polyurethane: Pelesene (tradename; Kasei-Upjohn), Paraplene (tradename; Nippon Elastoran);
 c. Olefinic thermoplastic elastomer: TPE (tradename; Sumitomo Chemical);
 d. Chlorinated-polyethylene-based thermoplastic elastomer: CMO (tradename; Dow Chemical), Daisorac (tradename; Osaka Soda);
 e. PoLyvinyl-chloride-based elastomer: Sumiflex (tradename; Sumitomo Bakelite);
 f. 1,2-polybutadiene: JSR (tradename; Japan Synthetic Rubber); and
 g. Polystyrene-based elastomer: Sorplene (tradename; Nippon Elastomer).

Figure 9:
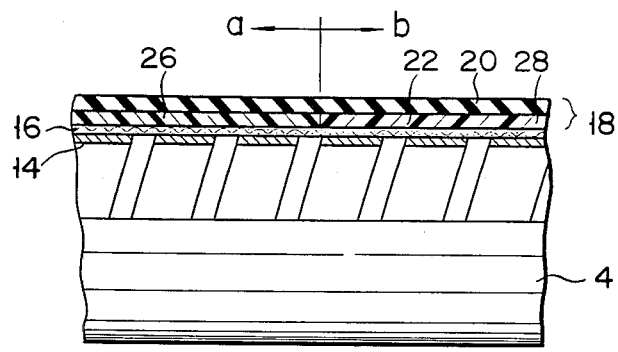
FIG. 9 is a sectional view showing part of an endoscopic flexible tube according to a first modification of the embodiment.

FIG. 9 shows a first modification according to the above-described embodiment of the present invention. In this modification, soft and rigid tube members 26 and 28 are used for inner layer 22 of sheath 18. Members 26 and 28, of different hardness, are connected in the middle of flexible tube portion 10, so that the flexibility of distal side (a) of portion 10 is different from that of proximal side (b).

According to the modification described above, the flexible tube has varied flexibility, as well as improved elasticity, thus further facilitating the insertion of the insertion section.

Figure 10:
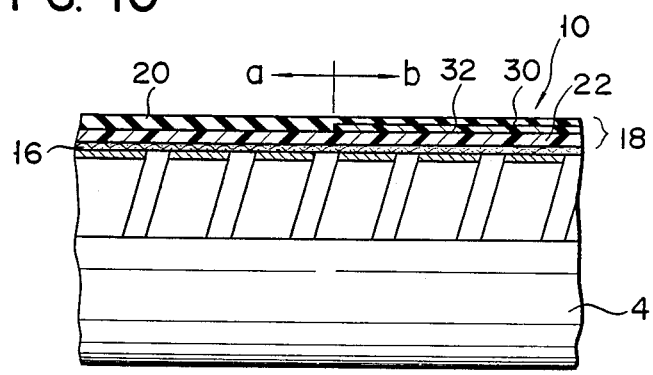
FIG. 10 is a sectional view showing part of an endoscopic flexible tube according to a second modification of the embodiment.

FIG. 10 shows a second modification according to the embodiment of the invention. In this modification, outer layer 20, at proximal side (b) of flexible tube portion 10, is formed of two layers 30 and 32 of different high-polymer materials. A rigid high-polymer is used for layer 32 on the inside. Thus, proximal side (b) is harder than distal side (a), so that the push-in force can be transmitted satisfactorily to the distal portion.

Figure 11:
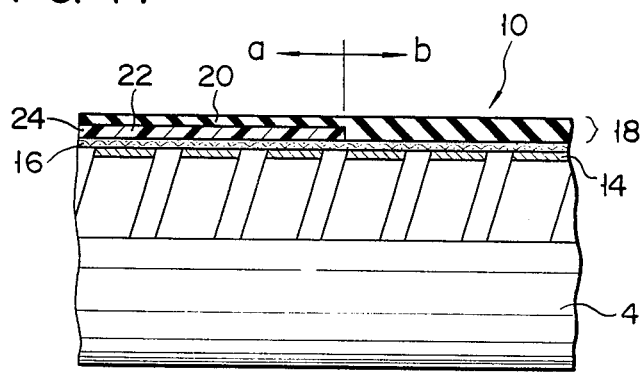
FIG. 11 is a sectional view showing part of an endoscopic flexible tube according to a third modification of the embodiment.

FIG. 11 shows a third modification according to the embodiment of the invention. In this modification, tube member 24, for use as inner layer 22, is force-fitted only into distal side (a) of flexible tube portion 10. Accordingly, distal side (a) is softer than proximal side (b), so that the push-in force can be transmitted satisfactorily to the distal portion, and the insertion section can be inserted with ease.

According to the present invention, as described in detail herein, high-polymer materials, constituting the sheath of the endoscopic flexible tube, never soak into the braid or spiral tube inside. Therefore, the restoring force of the braid and spiral tube cannot be hampered. In consequence, the elasticity of the flexible tube is improved, thus facilitating the insertion of the insertion section into the body cavity, so that the patient can be eased greatly of pain when he is subjected to an endoscopic diagnosis or examination.

What is claimed is:

1. An endoscopic flexible tube comprising:
    a spiral tube formed by transforming a belt-shaped metal member into a spiral;
    a braid formed of fibers intertwined like a net, and fitted on the outer peripheral surface of the spiral tube; and
    a sheath covering the outer peripheral surface of the braid, and having a multilayer structure composed of at least inner and outer layers, at least for part of its length,
    said inner layer including a tube member formed of a high-polymer material, and fitted on the outer peripheral surface of the braid, and
    said outer layer being formed by applying a molten high-polymer material to the outer peripheral surface of the tube member, for cross-linking.

2. The endoscopic flexible tube according to claim 1, wherein said tube member is formed of at least two tube members of different hardness, arranged in the longitudinal direction thereof.

3. The endoscopic flexible tube according to claim 1, wherein only part of the distal end portion of said sheath has the two-layer structure composed of the inner and outer layers.

4. The endoscopic flexible tube according to claim 1, wherein a third layer made of a relatively hard material is provided between an outer layer and an inner layer of a proximal end portion of said sheath, whereby the proximal end portion of said sheath has a three-layer structure, and is harder than a distal end portion of the sheath.

5. An endoscopic flexible tube comprising:
    a spiral tube formed by deforming a belt-shaped metal member in a spiral shape;
    a braid formed of fibers intertwined like a net, and fitted on the outer peripheral surface of the spiral tube; and
    a sheath covering the outer peripheral surface of the braid, and having a multilayer structure composed of an inner layer and an outer layer, at least for part of its length,
    wherein said inner layer is formed of at least two tube members made of high-polymer materials of different hardness, the tube members being arranged in the axial direction, and
    said outer layer is formed by applying a molten high-polymer material onto the outer peripheral surfaces of the tube members serving as said inner layer.

6. The endoscopic flexible tube according to claim 5, wherein a third layer made of a relatively hard material is provided between an outer layer and an inner layer of a proximal end portion of said sheath, whereby the proximal end portion of said sheath has a three-layer structure, and is harder than a distal end portion of the sheath.

* * * * *